United States Patent [19]
Caroselli et al.

[11] Patent Number: 5,602,178
[45] Date of Patent: Feb. 11, 1997

[54] BATH PRODUCTS CONTAINING MENTHYL LACTATE

[75] Inventors: Robert Caroselli, East Brunswick; Theodore Clemente, Jr., Belle Mead; Sandra E. Sandbeck, Metuchen, all of N.J.

[73] Assignee: Ciba-Geigy Corporation, Tarrytown, N.Y.

[21] Appl. No.: 339,377

[22] Filed: Nov. 14, 1994

[51] Int. Cl.⁶ .................... A01N 37/00; A61K 31/215
[52] U.S. Cl. .................................................. 514/529
[58] Field of Search .............................................. 514/529

[56] References Cited

U.S. PATENT DOCUMENTS

| | | |
|---|---|---|
| 4,272,516 | 6/1981 | Caldini et al. . |
| 4,929,446 | 5/1990 | Bartolucci et al. ............... 514/529 |
| 5,082,656 | 1/1992 | Hui et al. . |
| 5,227,163 | 7/1993 | Eini et al. ........................ 514/529 UX |
| 5,266,592 | 11/1993 | Grub et al. ...................... 514/529 UX |
| 5,362,494 | 11/1994 | Zysman et al. .................. 514/529 UX |

FOREIGN PATENT DOCUMENTS

| | | |
|---|---|---|
| 0582245 | 2/1994 | European Pat. Off. . |
| 9210988 | 7/1993 | WIPO . |
| 9321899 | 11/1993 | WIPO . |

OTHER PUBLICATIONS

Derwent Abstract 65128Y/37 of DT 2608226 Sep. 8, 1977.
Derwent Abstract 86–266837/41 of FR 2577922.
H & R Product Information (4 pages) concerning Frescolat (Menthyl Lactate).
Horner et al "Moglichkeiten und Grenzen photochemisch induzierter asymmetnischer Syntheses" Liebigs aun. Chem. 1232–1257 (1979).
Boireau et al "Hishly diastereoselecture reduction of (–) menthylphenylglyoxalate and (–) menthylpyruvate using new hindered lithiumtrial koxyaluminohydrides" Tetrahedren Assymmetry vol. 2, No. 8, pp. 771–774 (1991).

*Primary Examiner*—Paul F. Shaver
*Attorney, Agent, or Firm*—Marla J. Mathias; Karen G. Kaiser; Irving M. Fishman

[57] ABSTRACT

A method of achieving a relaxing, invigorating, tingling bath in the substantial absence of a menthol aroma, comprising incorporating into said bath a bath product formulation comprising menthyl lactate in an amount of about 0.5% to about 15% by weight of said formulation together with a bath product suitable carrier therefor.

5 Claims, No Drawings

BATH PRODUCTS CONTAINING MENTHYL LACTATE

FIELD OF THE INVENTION

The invention relates to the field of bath products. The invention further relates to the field of menthol esters.

BACKGROUND OF THE INVENTION

Menthol has been used in various topical preparations as a counterirritant, as an aesthetic agent (for its fragrance), and as a plasticizer in denture adhesive compositions. Unfortunately, the aroma of menthol has been a significant hinderance to its use in any meaningful amount other than where its fragrance is desired.

In compositions containing effective counter-irritant amounts of menthol (1.25% to 16% according to the FDA monograph for menthol), the aroma from menthol can be overpowering. In compositions used for cosmetic purposes (toiletries, etc), it is used in low concentrations, typically below 0.1% by weight. One of the major drawbacks in the use of menthol for a bath product is the overpowering aroma that remains.

Various menthol esters have been prepared. Most of these esters have disagreeable odors, making them truly unsuitable for use in a topical product. These odors are as disagreeable as, or more so than, menthol itself.

Menthyl lactate is a known compound available from Haarman & Reimer GmBH (Germany) under the name FRESCOLAT, Type ML. Two thirds of its molecular weight is attributable to the menthol moiety. The manufacturer's product literature indicates that it is a "cooling agent" and that it can be used in body care and cosmetic products in which "long lasting cooling and freshness are desired." According to the manufacturer, menthyl lactate is virtually odorless, not suffering from the "mint note" that is otherwise customary in the case of other menthol derivatives. The compound is recommended for use as a flavor in concentrations of 0.005 to 0.2% and in cosmetic and other external products in concentrations ranging from 0.2 to 2.0%. The maximum recommended amount of menthyl lactate as per the product literature is therefore 2.0% by weight, which would correspond 1.3% by weight of the menthol moiety. Nowhere is there any indication or suggestion that menthyl lactate should be used as a bath product.

OBJECTS OF THE INVENTION

An object of the invention is to provide a bath product which retains the desirable "tingling" of menthol, but does not have the disagreeable odor of menthol.

SUMMARY OF THE INVENTION

This and other objects of the invention can be achieved by using menthol lactate as the "active ingredient" in a bath formulation.

DETAILED DESCRIPTION OF THE INVENTION

The invention is a method of achieving an envigorating, relaxing, tingling sensation from a bath by incorporating into the bath, a suitable amount of a bath product containing menthyl lactate as the "active ingredient".

Menthyl lactate is the lactate ester of menthol and has the structural formula

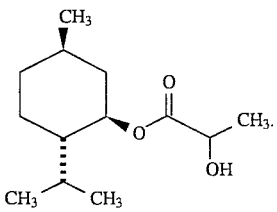

(I)

The compound is available commercially under the name Frescolat, Type ML from Haarmann & Reimer GmBH (Germany). It can also be readily made by processes known in the art by esterifying the hydroxy group of menthol with lactic acid.

For use in a bath product, menthyl lactate is present in compositions compatible with this use in amounts which range, for a bath salt, from about 0.5% to about 15% by weight of the total composition, preferably about 2.0% to about 10%, more preferably about 4.0% to about 8%, by weight of the total composition, most preferably about 6–7% of the total composition. Approximately, 20 to 40 grams of the bath salt formulation is added to a tub of about 30 to about 40 gallons of water (when full). Other formulations, such as bubble bath, bath softgels, bath oils, etc. should contain sufficient amounts of menthyl lactate so that when fully diluted in accordance with the product instructions, the same ranges of diluted menthyl lactate are obtained.

The remainder of the composition may be any suitable bath product carrier which is compatible with menthyl lactate.

Typical bath product formulations suitable for use in the present invention include, but are not limited to, bath salts, bath powders, bath oils, bath gels, etc.

Typical components for these products include, but are not limited to, a base material, fragrance, dispersing agent for the fragrance, colorant, preservative, etc.

As a general base for the solid forms (bath salts and bath gels) magnesium sulfate is generally used. However, suitable alternatives are known to those of ordinary skill in the art and include, but are not limited to, sodium sesquicarbonate, sodium borate, lithium chloride, potassium iodide, trace mineral complexes, Dead Sea salts, magnesium chloride, potassium chloride, sodium chloride, and calcium chloride. These materials can be used in the alternative or as combinations with each other as well as the magnesium sulfate. When magnesium sulfate is being used, it is preferable to use the heptahydrate. When magnesium sulfate heptahydrate is the base material in a bath salt or bath powder, it is typically present in about 53% to about 98.1% by weight of the formulation, preferably about 75% to about 95%, more preferably about 80% to about 90%, most preferably about 88% to about 89% of the formulation.

As a general base for the liquid forms (bath oils, bath lotions, etc) liquid petrolatum, glycerin, lanolin, polyethylene glycol, propylene glycol, and/or water in the range of 10–90% by weight, preferably 40–60% by weight is generally used. Alternatives include, without limitation, vitamin E oil, liquid parafin, and/or soybean oil, which can be used alone or in admixture with the foregoing bases.

Fragrances for use in the present invention can vary to any fragrance which may be desired as long as the fragrance itself is compatible with the other ingredients. Those of ordinary skill would be able to select appropriate scents for varying customer tastes. The fragrance is typically present in a bath powder or bath salt from about 0.3% to about 15.0%, preferably 0.4% to about 10%, more preferably about 0.5% to about 5%, still more preferably about 0.6% to about 0.75% of the formulation.

In formulating the solid forms, the fragrance typically needs a dispersant. The most desirable choice for this is magnesium carbonate. However, other materials which are suitable as alternatives or in combination with magnesium carbonate include, but are not limited to, maltodextrin and colloida silicon dioxide. Others will be apparent to those of ordinary skill. When needed, the dispersant is present in an amount of about 1.0% to about 15.0%, preferably about 2.0% to about 10%, more preferably about 3.0% to about 5.0%, most preferably about 3.7% to about 3.9% by weight of the formulation. Since the dispersant is present to disperse the fragrance, it is clear that hie amount of dispersant needed is also dependent upon the amount of fragrance being used. The person of ordinary skill in the art will be able to make appropriate adjustments to take this into consideration.

Colorants useful in the present invention are also only limited by being chemically compatible with the other ingredients. Typical choices are the aluminum and/or calcium lakes, iron oxides, soluble dyes, chlorophyllins, and combinations thereof, to name a few. Those of ordinary skill would be able to make suitable choices. Especially desirable is FD&C Blue #1 Aluminum Lake. The amount of colorant depends upon both the color desired and the intensity of that color. Typically the colorant can be present in amounts anywhere up to 10% by weight. With FD&C Blue #1 Aluminum Lake, a desirable shade and intensity are obtained with about 0.5% to about 1.2% by weight of the formulation being the Lake.

Additionally, solid dosage forms will typically need an anticaking agent to keep the salts or powders from agglomerating. A highly desirable material for this purpose is sodium aluminum silicate. Other alternative materials (which may also be used in combination with each other or with the sodium aluminum silicate) include, but are not limited to, colloidal silicon dioxide, talc, tribasic calcium phosphate, and corn starch. Others will also be known to those of ordinary skill. Typically this component, when needed, will be present in amounts of from about 0.1% to about 2.0%, preferably about 0.5% to about 1.0%, most preferably about 0.6% to about 0.8% by weight.

Preservatives suitable for use in the instant invention, without limitation, include propylparaben, methylparaben, benzyl alcohol, and or sodium bisulfite, and are used in amounts of from zero up to about 5%, preferably about 0.1% to about 1.0%, more preferably up to about 0.5% by weight.

Effervescent agents may also be included, if desired. This is especially advantageous if a compressed tabet or cake is desired as the formulation for precise measured dosing in a convenient form. Typical effervescent agents include, but are not limited to, sodium carbonate and sodium bicarbonate. Those of ordinary skill will have a wide range of such agents at their disposal.

Other agents which may be included in the formulations are sudsing agents and water softeners. Sudsing agents include, but are not limited to sodium lauryl sulfate, sodium lauryl sulfoacetate, disodium laureth sulfosuccinate. A typical water softener is sodium hexametaphosphate. Those of ordinary skill will know of alternatives for these products.

Each of the solid additives can be used in the solid forms, and all of the liquid and solid components can be used in the liquid forms. However, some of the liquid components, especially in the sudsing agent area, are very conducive to use in solid products. Those of ordinary skill in the formulation of bath products will be quite aware of these issues and be able to choose appropriate materials for the various types of formulations within the scope of the invention.

EXAMPLES

The following examples are intended to exemplify, but not to limit, the invention.

Example 1

A bath salt formulation is prepared having the following ingredients by the method set forth below:

| INGREDIENT | AMOUNT |
|---|---|
| Magnesium sulfate, heptahydrate | 88.44% |
| Menthyl lactate | 6.31% |
| Magnesium carbonate | 3.80% |
| spearmint/eucalyptus fragrance | 0.67% |
| FD&C Blue #1 Aluminum Lake | 0.08% |
| Sodium Aluminum Silicate | 0.70% |

The menthyl lactate is melted in a hot water bath. The fragrance is blended with the magnesium carbonate. Then the melted mentyl lactate is added to the blend and the mixture is blended. To this mixture, the magnesium sulfate, sodium aluminum silicate and the FD&C Blue #1 Aluminum Lake are added and the entire mixture is blended.

Example 2 Bath Oil

| INGREDIENT | AMOUNT |
|---|---|
| Menthyl Lactate | 6.0% |
| Mineral Oil | 90.5% |
| Laureth-4 | 2.0% |
| Preservative | 0.5% |
| Fragrance | 15.0% |

The menthyl lactate is dissolved in the mineral oil. The other ingredients are then added and the mixed.

We claim:

1. A method of achieving a relaxing, invigorating, tingling bath in the substantial absence of a menthol aroma, comprising incorporating into said bath a bath product formulation comprising menthyl lactate in an amount of about 0.5% to about 15% by weight of said formulation together with a bath product suitable carrier therefor.

2. A bath product comprising menthyl lactate in an amount of about 0.5% to about 15% by weight of said formulation and a carrier therefor.

3. The bath product of claim 2 which is selected from a bath salt, a bath powder, a bath oil, a bath gel, a bath bead, and a bubble bath.

4. The bath product of claim 2 wherein said carrier is magnesium sulfate heptahydrate.

5. The bath product of claim 2 further comprising at least one bath product additive selected from the group consisting of fragrances, colorants, dispersants, anti-caking agents, sudsing agents, water softeners, and effevescent agents.

* * * * *